United States Patent [19]

Kim et al.

[11] Patent Number: 5,179,208
[45] Date of Patent: Jan. 12, 1993

[54] PROCESS FOR PREPARING D-2-(6-METHOXY-2-NAPHTHYL)-PROPIONIC ACID AND INTERMEDIATE THEREOF

[75] Inventors: In O. Kim; Choong E. Song; Jae K. Lee, all of Seoul, Rep. of Korea

[73] Assignee: Korea Institute of Science and Technology, Seoul, Rep. of Korea

[21] Appl. No.: 889,232

[22] Filed: May 28, 1992

Related U.S. Application Data

[62] Division of Ser. No. 645,607, Jan. 25, 1991, Pat. No. 5,145,993.

[30] Foreign Application Priority Data

Oct. 19, 1990 [KR] Rep. of Korea ............... 16699/1990

[51] Int. Cl.$^5$ ......................................... C07D 263/04
[52] U.S. Cl. .................................................... 548/230
[58] Field of Search ........................................ 548/230

[56] References Cited

U.S. PATENT DOCUMENTS

| | | | |
|---|---|---|---|
| 3,651,106 | 3/1972 | Harrison | 260/429 R |
| 3,652,683 | 3/1972 | Harrison | 260/612 |
| 3,658,858 | 4/1972 | Harrison | 260/438.1 |
| 3,658,863 | 4/1972 | Harrison | 260/438.1 |
| 3,663,584 | 5/1972 | Alvarez | 260/429.9 |
| 3,683,015 | 8/1972 | Dyson | 260/520 |
| 3,686,238 | 8/1972 | Zaffaroni | 260/399 |
| 4,940,797 | 7/1990 | Jones et al. | 548/230 |

FOREIGN PATENT DOCUMENTS 2-262568 10/1990 Japan .

OTHER PUBLICATIONS

J. Am. Chem. Soc. 104 (1982) 1737.
J. Am. Chem. Soc. 73 (1951) 4199.

*Primary Examiner*—Paul J. Killos
*Attorney, Agent, or Firm*—Birch, Stewart, Kolasch & Birch

[57] ABSTRACT

A process for the prepaation of d-2-(6-methoxy-2-naphthyl)-propionic acid of formula (I) used as nonsteroid antipyretic analgesics, which comprises reacting oxazolidinone of formula (II) with 6-methoxy-2-naphthylacetchloride of formula (IV), methylizing [N-(γ-methoxy-2-naphthyl)acetyl]-oxazolidinone of formula (N), and reacting[N-(2S)-2-(6-methoxy-2-naphthyl)-propionyl]-oxazolidinone of formula (VI) in alkali metal hydroxy, and intermediate compound obtained by the process, [N-(6-methoxy-2-naphthyl)acetyl]-oxazolidinone of formula (V) and [N-(2S)-2-(6-methoxy-2-naphthyl)-propionyl]-oxazolidinone (VI)

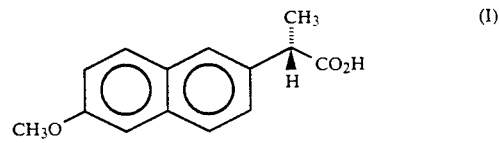

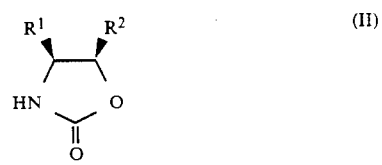

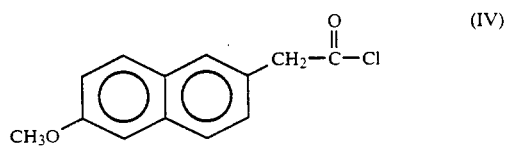

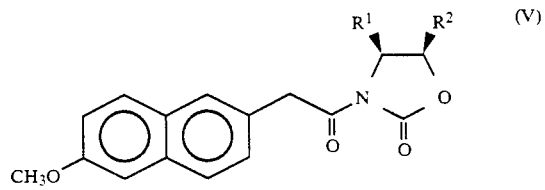

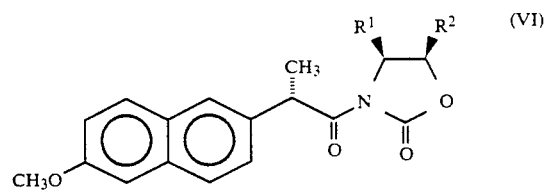

wherein $R^1$ is methyl, isopropyl, secondary-butyl, tert-butyl, benzyl, or phenyl group, and $R^2$ is hydrogen or phenyl group.

2 Claims, No Drawings

PROCESS FOR PREPARING D-2-(6-METHOXY-2-NAPHTHYL)-PROPIONIC ACID AND INTERMEDIATE THEREOF

This application is a divisional of copending application Ser. No. 07/645,607, filed on Jan. 25, 1991, the entire contents of which are hereby incorporated by reference, now U.S. Pat. No. 5,145,993.

BACKGROUND OF THE INVENTION

The present invention relates to a novel and improved process for preparation of d-2-(6-methoxy-2-naphthyl) propionic acid of formula (I) by means of a asymmetric synthesis method.

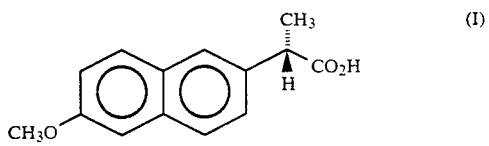

In d- and l-enantiomers of 2-(6-methoxy-2-naphthyl) propionic acid, particularly d-isomers can be used as nonsteriod antipyretic analgesics having an excellent anti-inflammatory, analgesic and antipyretic effects.

The general processes which are concerned with the present invention are described in U.S. Pat. Nos. 3,651,106, 3,652,683, 3,658,858, 3,658,863, 3,663,584, 3,686,238 and 3,683,015. According to these known processes d-isomers may be separated by preparing racemic mixtures of 2-(6-methoxy-2-naphthyl) propionic acid and by using alkaloid such as (+)-cinchonine, (−)-cinchonine and like.

Unlike the conventional process separating d-isomers from the racemic mixtures of 2-(6-methoxy-2-naphthyl) propionic acid, present invention is characterized in that only d-isomers are selectively prepared by means of method of asymmetric synthesis using oxazolilidinone compounds having the following formula (II) as a chiral auxiliary:

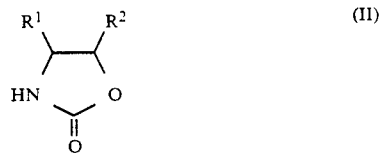

Wherein $R^1$ is $C_{1-8}$ alkyl or $C_{6-12}$ aryl of such as, for example, methyl, isopropyl, secondarybutyl, tert-butyl, benzyl, phenyl, group and like. $R^2$ is H, $C_{1-8}$ alkyl or $C_6$ aryl such as, for example, hydrogen, phenyl group. Also, wherein the absolute structure of chiral carbon atom (s) which is neighboring to $R^1$ is (S), when $R^2$ is not hydrogen atom (S), the absolute structure of the neighboring chiral carbon atom (S) is (R).

A method of the asymmetric synthesis of a substituted carboxylic acid derivatives can be found in the literature [J. Am. Chem. Soc. 104 (1982) 1737]. Accordingly, novel process for preparing compounds of general formula (I) in accordance with the present invention may be not necessary a complicated and cumbersome process for separating the existing d- and l-isomers or the racemization process for reusing an undesirable l-isomers. Thus, the present invention is economical and provides a novel and improved process for preparing.

Explaining now in detail the present invention, it is beginning by reacting oxazolidinone of formula (I) as a starting material with 6-methoxy-2-naphthylacet chrolide. Oxazolidinone of formula (II) is obtained by reacting p-aminoalcohol having optical activities which can be easily obtained from the natural substance, such as (S)-valinol (1R, 2S)-norephedrine (S)-phenylglycinol, (S)-allaninol, (S)-phenylallaninol, (S)-leucinol, (S)-isoleucinol, (S)-tert-leucinol and the like with phosgene or diethylcarbonate and the like. The detailed contents regarding to a process for preparing compounds of formula (II) are described fully in the literature [J. Am. Chem. Soc. 73 (195) 4199].

6-methoxy-2-naphthylacetehloride of formula (III) is obtained by reacting 6-methoxy-2-naphthylacetic acid of formula (III) with from 1 to 3 molar equivalents of thionyl chloride phosphorus tribromide oxalyl chloride and the like in a solvent such as benzene, diethylether, tetrahydrofuran, dichloromethane.

After terminating the reaction, the compound of formula (IV) is not separated and the solvent and the residual excess of halogenation. Reagent is only evaporated and removed and then used for the following reaction. The preferred halogenation reagent is oxallylchloride and the reaction is terminated by stirring the oxallyl chloride with the compound of formula (III) in the solvent such as tetrahydrofuran less than 24 hours at a room temperature.

After the metal salt of the compound of formula (II) is obtained by reacting the compound of formula (II) with the same equivalent of n-buthyllithium or sodium hydride and the like, novel [N-(6-methoxy-2-naphthyl)acethyl]-oxazolidinone compound is obtained by reaction of the resultant metal salt with the same equivalent of the compound of formula (IV) in succession.

In this case, suitable solvents include benzene, toluene, diethylether, tetrahydrofuran and the like. The reaction temperature is at a temperature of from about −30° to 20° C.

Novel [N-(2s)-2-(6-methoxy-2-naphthyl)-propionyl-]oxazolidinone compound of formula (VI), after reacting [N-(6-methoxy-2-naphthyl)acethyl]-oxazolidinone compound of formula (V) with the same equivalent of a base such as lithiumisopropylamide or sodium bistrimethylsilylamide and a like at the temperature of the range from −80° C. to 0° C., is obtained by reacting the resultant reaction solution with an excess of quantity of methane iodide or dimethyl sulfate. The yield of the compound of formula (VI) is more than 90%, and the optical yield is also more than 98%.

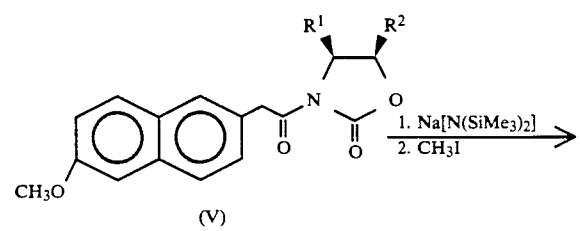

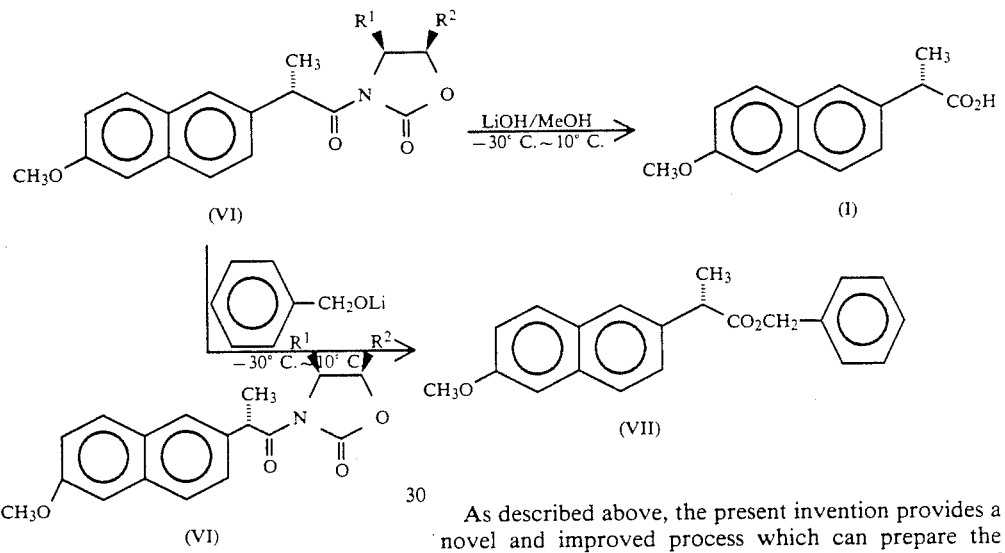

When d-2-(6-methoxy-2-naphthyl)propionic acid of formula (I) is prepared from [N-(2s)-2-(6-methoxy-2-naphthyl)-propionyl]oxazolidinone compound of formula (VI), the acid can be prepared by two methods, the one method being obtained by reacting the compound of formula (VI) directly in the alkali metal hydroxide and alcohol water solution and the like at the temperature from −30° to 10° C. for 1 hour, the other method being prepared the ester compound of formula (VI) by reacting the compound of formula (VI) with alkali metal alkoxide and the like at the temperature of −30° C. to 10° C. for 1 hour acid then obtaining the compound of formula (I) from these ester compounds. The resultant compound of formula (I) have the optical purity of more than 99%, and particularly oxazolidinone compound of formula (II) used as chirol auxiliary is not dissolved and not racemated thereby complexly being recovered.

As described above, the present invention provides a novel and improved process which can prepare the compounds of formula (I) in very high yield by way of novel compounds of formulas (V) and (VI) and selectively through simple stages, otherwise than the previous processes according to the separation process of d, l-isomers.

In order to promote understanding of the present invention, the reaction scheme for preparing d-2-(6-methoxy-2-naphthyl)propionic acid is presented as follow.

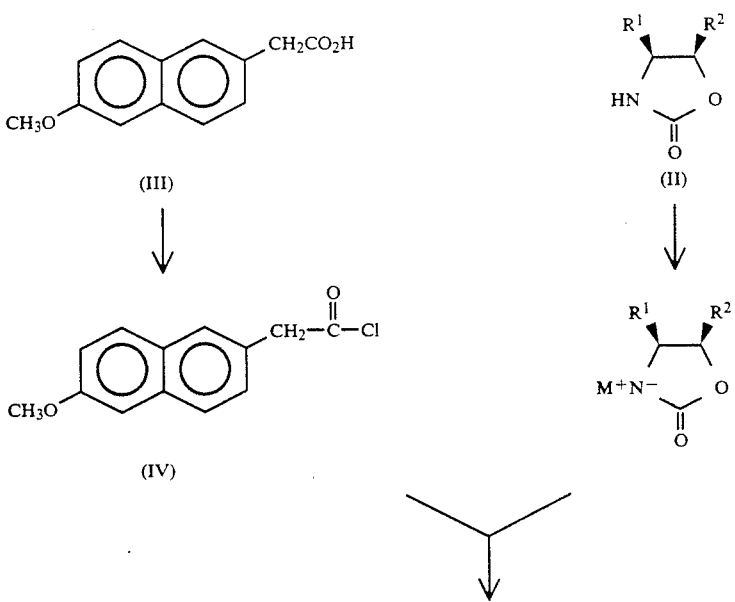

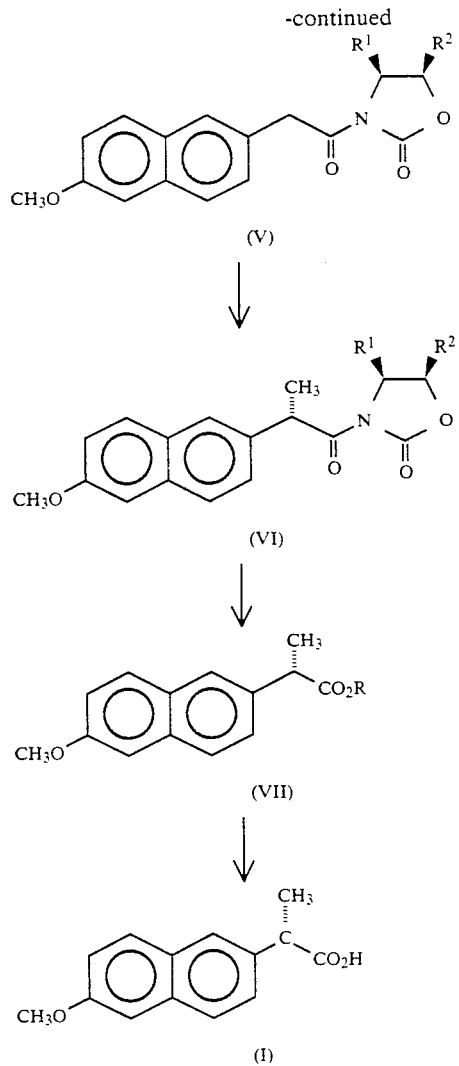

(V)

(VI)

(VII)

(I)

Referring to the examples, the present invention is explained in detail as follows:

The following reactions were proceeded under the nitrogen air, unless otherwise mentioned.

EXAMPLE 1

Preparation of 2-(6-methoxy-2-naphthyl)-acetyl chloride (IV)

To a solution dissolved 21.3 g (0.1 mol) of (6-methoxy-2-naphthyl)acetic acid in tetrahydrofuran anhydride (200 ml) was slowly added 19.0 g (0.15 mol) of oxalyl chloride and 1 ml of dimethylformamic at 0° C. After stirring at the room temperature for 15 hours, solvent and an excess of oxalyl chloride were removed to nearly quantitatively yield (6-methoxy-2-naphthyl)-acetyl chloride as product.

nmr (60 MHz, CDCl$_3$): δ3.75 (s, 3H, —OCH$_3$), 4.22 (s, 2H, —CH$_2$—), 7.0–7.8 (Naphthyl ring protons)

EXAMPLE 2

Preparation of [N-(6-methoxy-2-naphthyl)acetyl]-(4S,5R)-4-methyl-5-phenyl-2-oxazolidinone (V)

To a solution dissolved 17.2 g (0.1mol) of (4S,5R)-(+)-4-methyl-5-phenyl-oxazolidinone in tetrahydrofuran (200 ml) was slowly added 66 ml of n-butyl lithium (1.5 M hexane solution) at the inner temperature of −15° C. and then reacted at the same temperature for about 1 hour. To the reaction mixture was slowly added a solution dissolved 24 g of (6-methoxy-2-naphthyl)-acetyl chloride of Example 1 in tetrahydrofuran anhydride (70 ml) at the inner temperature of 0° C. and then stirred to react for about 1 hour. If the reaction was completed, the resulting solution was poured into saturated aqueous ammonium chloride solution (500 ml), the organic layer was extracted with ethyl ether (150 ml), the ethyl ether layer was dried with sodium sulfate anhydride and then filtered, and the solvent was evaporated under reduced pressure and removed to yield 34 g of [N-(6-methoxy-2-naphthyl)-acetyl]-(4S,5R)-4-methyl-5-phenyl-2-oxazolidinone as white solid (yield 91%).

nmr (200 MHz, CDCl$_3$)δ0.88 (d, J=6.6Hz, 3H, —NCH(CH$_3$)—), 3.90 (s, 3H, —OCH$_3$), 4.43 (s, 2H, —CH$_2$C(O)—), 4.75 (p from q*d, J=6.7 Hz, 1H, —NCH(CH$_3$)—), 5.63 (d, J=7.3 Hz, 1H, —CH(C$_6$H$_5$)O), 7.0–7.8 (m, 5 H, —CH(C$_6$H$_5$)O—)

elementary analysis C$_{23}$H$_{21}$NO$_4$ MW 375.43 g/mol
theoretical value C 73.58%, H 5.64%, N 3.72%
experimental value C 73.10%, H 5.69%, N 3.31%

EXAMPLE 3

Preparation of
[N-(6-methoxy-2-naphthyl)acetyl]-(4S)-4-isopropyl-2-oxazolidinone (V)

To a solution dissolved 12.9 g (0.1 mol) of (4S)-4-isopropyl-2-oxazolidinone in tetrahydrofuran (200 ml) was slowly added 63 ml of n-butyl lithium (1.5 M hexane solution) at the inner temperature of −15° C. and then reacted at the same temperature for about 1 hour. To the reaction mixture was slowly added a solution 24 g of (6-methoxy-2-naphthyl)-acetyl chloride in tetrahydrofuran (70 ml) at the inner temperature of 0° C. and then stirred to react for about 1 hour. If the reaction was completed, the resulting solution was poured into saturated aqueous ammonium chloride solution (500 ml), the organic layer was extracted with ethyl ether (150 ml), the ethyl ether layer was dried with sodium sulfate anhydride and then filtered, and the solvent was evaporated under reduced pressure and removed to yield 31 g of [N-(6-methoxy-2-naphthyl)-acetyl[-(4S)-isopropyl-2-oxazolidinone as white solid (yield 95%).

nmr (200 MHz, CDCl$_3$)δ0.77 (d, J=6.9 Hz, 3H, —CH(CH$_{3A}$)CH$_{3B}$), 0.86 d, J=7.1 Hz, 3H, —CH(CH$_{3A}$)CH$_{3B}$), 2.29–2.39 (sym. m, 1H, —CH(CH$_3$)$_2$), 3.90 (s, 3H, —OCH$_3$), 4.10–4.30 (m, 3H, —NCH(i-Pr)CH$_2$O). 4.32 and 4.35 (AB-spin system, J$_{AB}$=15.3 Hz, 2H, —CH$_A$H$_B$C(O)—), 7.0–7.7 (m, 6H, Naphthyl ring protons)

EXAMPLE 4

Preparation of [N-(2S)-2-(6-methoxy-2-naphthyl)propionyl]-(4S,5R)-4-methyl-5-phenyl-oxazolidinone (VI)

18.8 g (0.05 mol) of [N-(6-methoxy-2-naphthyl)-acetyl](4S,5R)-4-methyl-5-phenyl-2-oxazolidinone was dissolved in 150 ml of tetrahydrofuran anhydride, the solution was maintained at the inner temperature of −70° C., and stirred to react, with slowly adding 50 ml of sodium bistrimethyl silylamide (1.0 M tetrahydrofuran solution). After reacting for about 30 minutes, to this solution was slowly added 11.4 g of methane iodide at 0° to −5° C. and reacted for 10 hours continuously. The reaction material was poured into saturated aqueous ammonium chloride solution (500 ml), the organic layer was extracted with ethyl ether and dried with sodium sulfate anhydride, and the solvent was evaporated under reduced pressure and then removed. The residue was used the column chromatography to yield 17.8 g of pure 2-(6-methoxy-2-naphthyl)propionyl (4S,5R)-(+)-4-methyl-5-phenyl2-oxazolidinone (yield 91%).

nmr (200 MHz, CDCl$_3$) δ0.94 (d, J=6.8 Hz, 3H, —NCH(CH$_3$)—), 1.58 (d, J=6.9 Hz, 3H, —CH(CH$_3$)—C(O)—), 3.90 (s, 3H, —OCH$_3$), 4.66 (p from q*d, J=6.7 Hz, 1H, —NCH(CH$_3$)—), 5.28 (q, J=6.8 Hz, 1H, —CH(CH$_3$)C(O)—), 5.43 (d, J=7.0 Hz, 1H, —CH(C$_6$H$_5$)O—), 7.0–7.8 (m, 11H, —CH(C$_6$H$_5$)O— and Naphtyl ring protons)

EXAMPLE 5

Preparation of [N-(2S)-2-(6-methoxy-2-naphthyl)propionyl[-(4S)-(4)-isopropyl-2-oxazolidinone (VI)

16.3 g (0.05 mol) of [N-(6-methoxy-2-naphthyl)-acethyl[-(4S)-4-isopropyl-2-oxazolidinone was dissolved in 150 ml of tetrahydrofuran anhydride, the solution was maintained at the inner temperature of −70° C., and stirred to react, with slowly adding sodium bistrimethylsilyl amide (1.0 M tetrahydrofuran solution). After reacting for about 30 minutes, to this solution was slowly added 114 g of methane iodide at 0° C. to −5° C. and reacted for 10 hours continuously. The reaction material was poured into saturated aqueous ammonium chloride solution, the organic layer was extracted with ethyl ether and dried with sodium sulfate anhydride and the solvent was evaporated under reduced pressure and then removed. The residue was used the column chromatography to yield 15.5 g of pure 2-(6-methoxy-2-naphthyl)propionyl-(4S)-4-isopropyl-2-oxazolidinone (yield 91%).

nmr (200 MHz, CDCl$_3$)δ0.97 (d, 7.1 Hz, 6H, —CH(CH$_3$)$_2$), 1.58 (d, 6.9 Hz, 3H, —CH)CH$_3$)C(O)—), 2.45 (sym. m, 1H, —CH(CH$_3$)$_2$), 3.39 (s, 3H, —OCH$_3$), 4.0–4.2 (m. 2H, —CH$_2$O—), 4.3–4.4 (m, 1H, —NCH(i-Pr)CH—), 5.28 (q, J=6.9 Hz, 1H, —CH(CH$_3$)C(O)—), 7.0–7.8 (m, 6H, Napthyl ring protons)

elementary analysis C$_{20}$H$_{23}$NO$_4$ MW 341.41 g/mol
theoretical value C 70.36%, H 6.79%, N 4.10%
experimental value C 70.40%, H 6.79%, N 4.05%

EXAMPLE 6

Preparation of d-2-(6-methoxy-2-naphthyl) propionyl benzyl ester (VII)

To a solution of 7.78 g (0.02 mol) of [N-2-(s)-(6-methoxy-2-naphthyl)propionyl[-(4S,5R)-4-methyl-5-phenyl-2-oxazolidinone in 100 ml of tetrahydrofuran anhydride was slowly added a solution mixing 4.33 g of benzylalcohol with n-butyl lithium (5 M hexane solution) at −10° C. and then stirred to react for about 2 hours. The reaction solution was poured into 500 ml of water, the organic layer was extracted with ethyl ether (150 ml), the ethyl ether layer was tried with sodium sulfate anhydride, and the solvent was evaporated under reduced pressure to yield 5.8 g of white solid products (yield 94%).

nmr (60 MHz, CDCl$_3$)δ1.5 (d, J=7.2 Hz, —CH$_9$CH$_3$)—), 3.9 (s, 3H, —OCH$_3$), 5.2 (s, 2H, —CH$_2$—C$_6$H$_5$), 7.3 (s, 5H, —CH$_3$—C$_6$H$_5$), 7.0–7.8 (m, 6H, Naphtyl ring protons)

EXAMPLE 7

Preparation of d-2-(6-methoxy-2-naphthyl) propionic acid (I)

To a solution 3.9 g (0.01 mol) of [N-2-(s)-(6-methoxy-2naphthyl)propionyl]-(4S,5R)-4-methyl-5-phenyl-2-oxazolidinone in 50 ml of methanol was added 1 N LiOH aqueous solution at 0° C. and then stirred to react for 1 hour. The reaction solution was acidified with chloric acid and the produced crystal was filtered and dried to yield 1.4 g of 2-(6-methoxy-2-naphthyl)propionic acid as white solid.

nmr (60NHz, CDCl$_3$)δ3.7 (s, 2H, —CH—), 3.9 (s, 3H, —OCH$_3$), 7.0–7.8 (m, 6H, Naphtyl ring protons)

EXAMPLE 8

Preparation of d-2-(6-methoxy-2-naphthyl)propionic acid (I)

To a solution 3.1 g (0.01 mol) of 2-(6-methoxy-2-naphthyl)-propionyl benzylester in 100 ml of ethyl alcohol was added 0.2 g of 10% palladium activated carbon and then stirred to react in the hydrogen reduction reactor (hydrogen pressure 30 psi) for 1 to 2 hours. After the reaction was completed, palladium activated carbon was removed by filteration and the ethyl alcohol was evaporated under reduced pressure and removed to yield 2 g of 2-(6-methoxy-2-naphthyl)propionic acid as white solid (yield 93%).

nmr (60 MHz, CDCl$_3$)δ3.7 (s, 2H, —CH—), 3.9 (s, 3H, —OCH$_3$), 7.0–7.8 (m, 6H, Naphtyl ring protons)

[α]= +65.8° (c=1, CHCl$_3$), optical purity is more than 99%

What is claimed is:

1. Novel [N-(6-methoxy-2-naphthyl)acetyl]-oxazolidinone represented by the formula

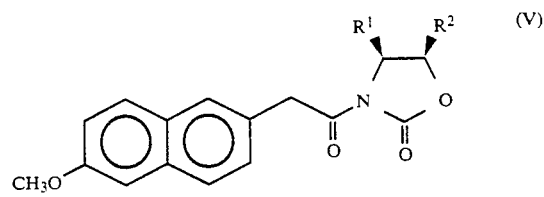

wherein R$^1$ is methyl, isopropyl, secondary-butyl, tert-butyl or benzyl, phenyl group, R$^2$ is hydrogen or phenyl group.

2. Novel [N-(2S)-2-(6-methoxy-2-naphthyl)propionyl] oxazolidinone represented by the formula

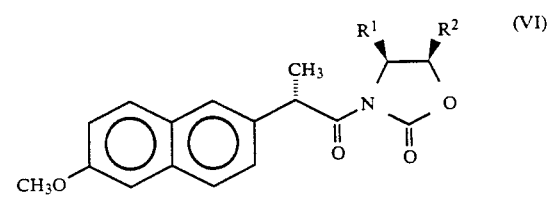

wherein R$^1$ is methyl, isopropyl, secondary-butyl, tert-butyl benzyl, phenyl group, R$^2$ is hydrogen or phenyl group.

* * * * *